(12) United States Patent
Trainin et al.

(10) Patent No.: US 6,544,529 B1
(45) Date of Patent: Apr. 8, 2003

(54) **ISOLATED STRAINS OF *STAPHYLOCOCCUS AUREUS* AND VACCINES MANUFACTURED THEREFROM**

(75) Inventors: Ze'ev Trainin, Tel-Aviv (IL); Gabriel Leitner, Mazkeret Batya (IL); Eugenia Liubashewsky, Bnei Aish (IL)

(73) Assignee: Maabarot Products Ltd., Kibbutz Maabarot (IL)

( * ) Notice: Subject to any disclaimer, the term of this patent is extended or adjusted under 35 U.S.C. 154(b) by 0 days.

(21) Appl. No.: 09/582,692

(22) PCT Filed: Dec. 29, 1998

(86) PCT No.: PCT/IL98/00627

§ 371 (c)(1),
(2), (4) Date: Sep. 1, 2000

(87) PCT Pub. No.: WO99/33954

PCT Pub. Date: Jul. 8, 1999

(30) Foreign Application Priority Data

Dec. 31, 1997 (IL) .................................................. 122829

(51) Int. Cl.[7] ...................... A61K 39/085; A61K 39/00; A61K 39/116; A61K 45/00
(52) U.S. Cl. .................. 424/243.1; 424/184.1; 424/203.1; 424/237.1; 424/278.1
(58) Field of Search ............................ 424/243.1, 278.1, 424/237.1, 184.1, 203.1

(56) References Cited

U.S. PATENT DOCUMENTS 4,425,330 A * 1/1984 Norcross et al. .............. 424/92

OTHER PUBLICATIONS

Sompolinsky et al, Journal of Clinical Microbiology, Nov. 1985, p. 828–834.*
Poutrel et al, Journal of Clinical Microbiology, Jan. 1988.*
Nickerson et al, Journal of Dairy Science, 76: 1290–1297.*
Guidry et al, Veterinary Microbiology, 59:(1997) 53–58.*

* cited by examiner

*Primary Examiner*—Mark Navarro
*Assistant Examiner*—Vanessa L Ford
(74) *Attorney, Agent, or Firm*—Snell&Wilmer LLP

(57) ABSTRACT

The invention provides antigenic compositions for the vaccination of an animal against bovine mastitis caused by infection with *Staphylococcus aureus*. The invention also provides methods for stimulating an animal's immune system to respond to antigens derived from selected strains of *Staphylococcus aureus* by administering the antigenic compositions of the invention to the animal.

10 Claims, 4 Drawing Sheets

Immunoblot of mice sera against BSs antigen before and after vaccination with *S. aureus* vaccine.

*Fig 1*

Time table of the two vaccinated and
challenged trials in cow's study

Trial 1.

-60 -25 -13  0  13  22  37  43  57  63  65  66  70  73  78  84
 *   *   *  *   *   *   *   *   *   *   *   *   *   *   *   *
         Vacc.     Boost    "Volcani"  Challenge            Histology Trial 2.

-30 -5  0  9  21  36  45  56      69  72  77  78  79  84  91  98
 *   *  *  *   *   *   *   *       *   *   *   *   *   *   *   *
         Vacc.    Boost  Boost  "Volcani"      Challenge        Histology \* Test: Bacteriology, SCC, Differentiate count, NAGase, and Antibody in blood and milk

*Fig 2*

ISOLATED STRAINS OF STAPHYLOCOCCUS AUREUS AND VACCINES MANUFACTURED THEREFROM

This application claims priority to a 371 PCT/IL98/00627, filed Dec. 29, 1998.

FIELD OF THE INVENTION

The present invention relates generally to bovine mastitis infections caused by Staphylococcus aureus and, more particularly, to vaccines derived from selected strains of Staphylococcus aureus.

BACKGROUND

Bovine mastitis is the most important infectious disease affecting both the quality and quantity of milk production. Staphylococcus aureus (i.e., "S. aureus") is the prime agent causing bovine mastitis, and it is difficult to eliminate. In different countries, the prevalence of S. aureus mastitis ranges from 10% to 40% of all cows. The infected animals may serve as reservoirs of infection endangering other dairy cattle in the herd (Fox, L. K. and Hancock, D. 1989, "Effects of segregation on prevention of intramammary infection by Staphylococcus aureus", J. Dairy Sci. 72:540–544).

Recent estimates suggest that the annual production losses due to S. aureus are over 15 million dollars in Israel and over 2 billion dollars in the USA. The prevalence of S. aureus mastitis in dairy cattle raises several concerns. This bacterium can cause severe damage to milk-synthesizing tissues, drastically reducing milk production and altering milk composition. For more information on bovine mastitis and its effects, see, for example: (1) Oliver, S. P., Sordillo, L. M, 1988, "Udder health in the periparturient period", J Dairy Sd. 71:2584–2606; (2) Postle, D. S., Roguinsky, M., Poutrel, B., 1978, "Induced Staphylococcal infections in the bovine mammary gland", Am J Vet Res. 39:29–35; (3) Sordillo, L. M., Nickerson, S. C and Akers, R. M., 1989, "Pathology of mastitis during lactogenesis: Relationships with bovine mammary structure and function", J. Dairy Sci. 72: 228–240; (4) Watson, D. L., McColl, M. L., Davies, H. I., 1996, "Field trial of a Staphylococcal mastitis vaccine in dairy herds: clinical, subclinical and microbiological assessments", Aust. Vet. J. 74:447–450.

Depending on the duration and the severity of the infection, the productive performance of dairy cattle may be diminished permanently. Therefore, the development of effective methods of controlling S. aureus mastitis will increase profitability to dairy producers by reducing costs. So far, post-milking teat disinfection and antibiotic therapy are the only widely accepted methods of mastitis control (National Mastitis Council, 1987, "Current concepts of bovine mastitis", Arlington, Va.).

These methods are not cost-effective due to milk loss during and after antibiotic therapy. Moreover, antibiotic therapies formulated for intramammary use are generally unsuccessful in eliminating existing S. aureus infections or preventing the establishment of chronic diseases (Ziv, G., 1995, "Treatment of Mastitis: An overview of progress during the last ten years", Proc. The 3rd Internal Mastitis Seminar, Tel Aviv, Israel 2–12).

There is also a growing concern over the presence of drug residues in the food supply as a consequence of these procedures. To date, culling chronically infected cows is often the only practical means of eliminating S. aureus from a herd.

Vaccination is a logical approach for controlling infectious diseases in food producing animals. However, the paucity of information regarding relevant antigens remains a major deterrent to successful immunization against S. aureus mastitis. To our knowledge, the known, commercially available S. aureus vaccines have shown limited efficacy under field conditions. See, for example:

In the USA:

1) Nickerson, S. C., Owens, W. E., Bodie, R. L, 1993, "Effect of a Staphylococcus aureus bacterin on serum antibody, new infection, and mammary histology in non lactating dairy cows", J. Dairy Sci., 76:1290–1297;

2) Sears, P. M., Norcross. N. L., Kenny, K., Smith, B., Gonzalez, R. N., Romano, M. N., 1990, "Resistance to Staphylococcus aureus infections in staphylococcal vaccinated heifers", Proc. Internatl. Symp. Bovine Mastitis, Indianapolis, Ind., p. 69.

3) Sordillo, L. M., Nickerson, S. C and Akers, R. M., 1989, "Pathology of mastitis during lactogenesis: Relationships with bovine mammary structure and function", J. Dairy Sci., 72: 228–240; and 4) Yoshida K., Ichiman, Y., Narikawa, S., Evans, G. B., 1984, "Staphylococcal capsular for preventing mastitis in two herds in Georgia", J. Dairy Sci., 67:620–627.

In Australia:

1) Watson, D. L., 1984, "Evaluation of attenuated, live staphylococcal mastitis vaccine in lactating heifers", J. Dairy Sci., 67:2608–2613;

2) Watson, D. L., Schwartzkoff, C. L., 1990, "A field trial to test the efficacy of a staphylococcal mastitis vaccine in commercial dairies in Australia", International Symposium on Bovine Mastitis, National Mastitis Council, Arlington, 73–76;

3) Watson, D. L., 1992, "Vaccination against experimental staphylococcal mastitis in dairy heifers", Res. Vet. Sci., 53:346–353; and 4) Watson, D. L., McColl, M. L., Davies, H. I., 1996, "Field trial of a Staphylococcal mastitis vaccine in dairy herds: clinical, subclinical and microbiological assessments", Aust. Vet. J., 74:447–450.

In Norway:

1) Nordhaug, M. L., Nesse, L. L., Norcross, N. L., Gudding, R., 1994, "A field trial with an experimental vaccine against Staphylococcus aureus mastitis in cattle. I. Clinical parameters", J Dairy Sci., 77:1267–1275;

2) Pankey, J. W., et al., 1985, "Evaluation of protein A and a commercial bacterin as vaccines against Staphylococcus aureus mastitis by experimental challenge", J. Dairy Sci., 68:726–731; and 3) Yoshida K., Ichiman, Y., Narikawa, S., Evans, G. B., 1984, "Staphylococcal capsular for preventing mastitis in two herds in Georgia", J. Dairy Sci., 67:620–627.

For the most part, these conventional vaccines have not prevented the disease and show only a marginal benefit in ameliorating the severity and duration of clinical symptoms of S. aureus mastitis. Traditional S. aureus mastitis vaccines have included killed or attenuated bacteria, toxoids, and cell wall extracts from selected laboratory or field strains. See: (1) Nickerson, S. C.; (2) Sears, P. M.; (3) Watson, D. L. 1984; and (4) Watson, D. L., 1992; as cited above.

These previous attempts have not considered the significant variation among the different strains of S. aureus which cause mastitis.

Attempts to solve this problem are described in U.S. Pat. No. 4,840,794. However this solution has not been satisfactory.

It is, therefore, desirable to develop a vaccine which would overcome the above disadvantages and would prevent the occurrence of bovine mastitis infection or at least control such infections to a large extent.

BRIEF DESCRIPTION OF THE DRAWINGS

Additional aspects of the present invention will become evident upon reviewing the non-limiting embodiments described in the specification and the claims taken in conjunction with the accompanying figures, wherein:

FIG. 1 is an immunoblot of mice sera against BS449 antigen before and after the administration of an S. aureus vaccine in accordance with the invention;

FIG. 2 is a time table of two studies involving an S. aureus vaccine in accordance with the invention;

DETAILED DESCRIPTION OF EXEMPLARY EMBODIMENTS

Figure 3:
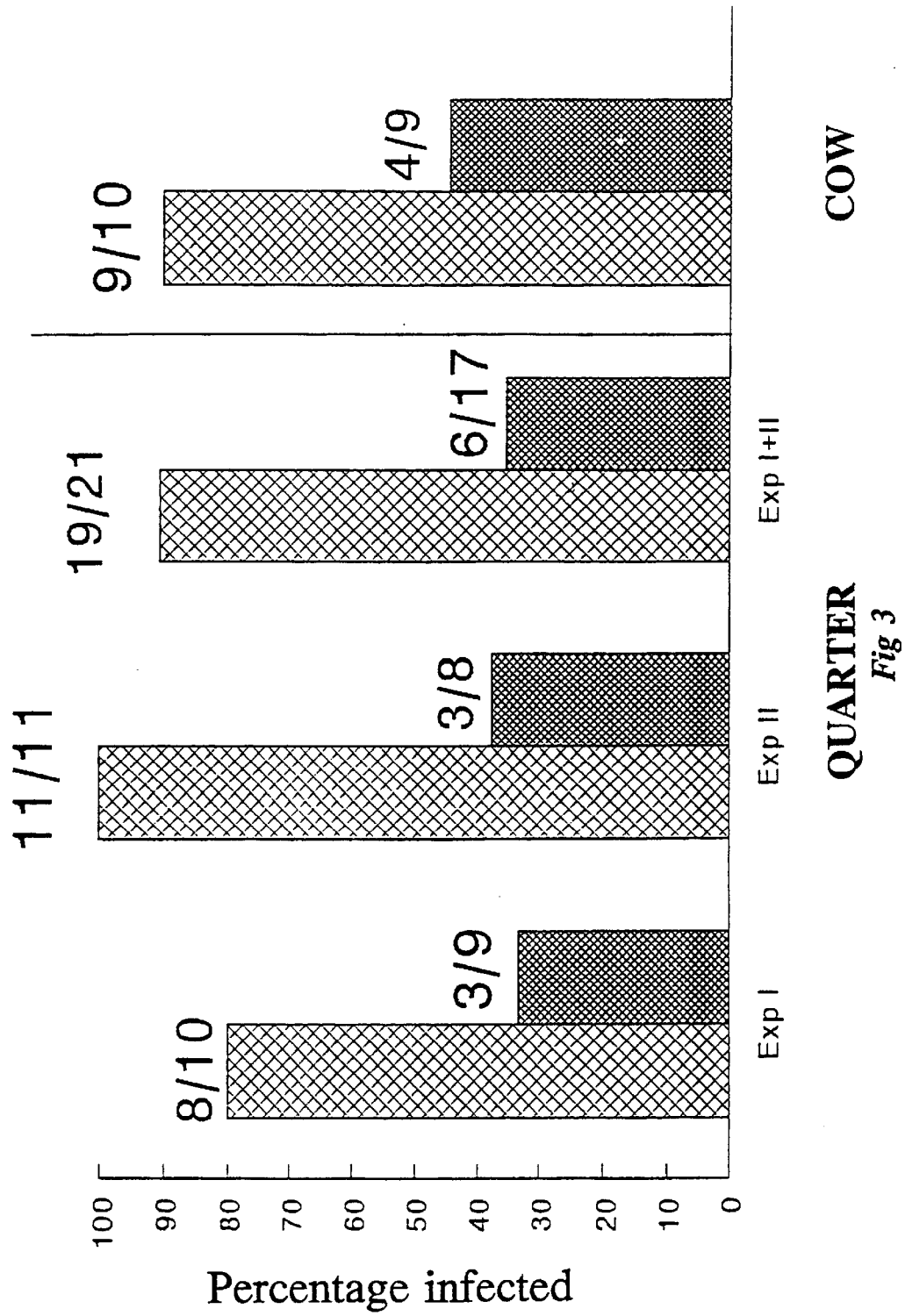
FIG. 3 is a graphical depiction of results of the studies that are the subject of FIG. 2.

It has been shown that a vaccine which would overcome the above disadvantages and would prevent the occurrence of bovine mastitis infection or is at least control such infections to a large extent cannot be prepared from known strains of S. aureus, and, therefore, new strains had to be isolated.

In one aspect, the present invention provides the following three field strains of S. aureus, either separately or in combination: strain BS449 (i.e., BS); strain ZO3984 (i.e., ZO); and strain VLVL8407 (i.e., VL). For convenience, these strains are collectively referred to herein as "the S. aureus strains". Each of the three strains may be characterized by the following basic features:

Strain BS449: β-hemolytic; coagulase positive; and phage type 81;

Strain ZO3984: β-hemolytic; coagulase positive; and phage type 3/A, 3/C, 55, and 71; and Strain VLVL8407: non-hemolytic; coagulase positive; and phage untypable.

Further biochemical and enzymatic features are shown in Table I. Antibiograms are shown in Table II.

TABLE I

Biochemical and Enzymatic Characterization

| | VLVL8407 | ZO3984 | B5449 |
|---|---|---|---|
| Phage type | − | 3/A, 3/C, 55, 71 | 81 |
| Hemolysis | − | β | β |
| Coagulase | + | + | + |
| GLU Glucose | + | + | + |
| FRU Fructose | + | + | + |
| MAL Maltose | + | + | + |
| LAC Lactose | + | + | + |
| TRE Trehalose | + | + | + |
| MAN Manitol | + | + | + |
| RAF Rafinose | + | − | − |
| RIB Ribose | − | − | − |
| CEL Celobiose | − | − | − |
| NIT Nitrates (reduction) | + | + | + |
| VP (Actoin Production) | + | + | + |
| βGal βGalctosidase | − | − | − |
| ArgA Arginine Arylamidase | − | − | − |
| PAL Alkaline Phosphatase | + | + | + |

TABLE I-continued

Biochemical and Enzymatic Characterization

| | VLVL8407 | ZO3984 | B5449 |
|---|---|---|---|
| PyrA Pyrrolidonyl Arylamidase | + | + | + |
| NOVO Novobiocin (Resistance) | − | + | − |
| Fermentation: | | | |
| SAC Sucrose | + | + | + |
| NAG N-Acetyl-glucosamine | + | + | + |
| TUR Turanose | + | + | + |
| ARA Arbinose | − | − | − |
| βGUR βGlucuronidase | − | − | − |
| URE Urease | + | − | + |
| ADH Arginin dihydrolase | + | + | + |
| ODC Ornithine decaboxilase | − | − | − |
| ESC Esculine (hydrolysis) | − | − | − |

TABLE II

Antibiograms

| | ZO3984 | VLVL8407 | B5449 |
|---|---|---|---|
| METHICILLIN (N)* | − | − | − |
| PENICILLIN (P) | − | − | − |
| OXYTETRACYCLINE (T) | ± | − | − |
| ERYTHROMYCIN (E) | ± | + | + |
| CEPHALOTHIN (CR) | + | + | + |
| NOVOBIOCIN (NB) | + | + | ± |
| NORFLOXACIN (NEF) | + | + | + |
| SXT (SXT) | − | − | − |

*METHICILLIN represents CLOXACILLIN and NAFCILLIN

The S. aureus strains were deposited under the terms of the Budapest Treaty on Dec. 16, 1997 with the Collection Nationale de Cultures de Microorganismes (CNCM), Institut Pasteur, 25 Rue du Docteur Roux, F-75724 Paris CEDEX 15. The deposited strains were assigned the following registration numbers:

| BS 449 (449) | I - 1950 |
| ZO 3984 (84) | I - 1951 |
| VLVL 8407 | I - 1952 |

The deposit represents a biologically pure culture of each deposited strain. Access to the cultures will be available during pendency of the patent application to one determined by the Commissioner to be entitled thereto under 37 CFR 1.14 and 35 USC 122. All restrictions on the availability of the cultures to the public will be irrevocably removed upon the granting of a patent based upon the application. However, it should be understood that the availability of the cultures on deposit does not constitute a license to practice the subject invention in derogation of the patent rights granted.

The S. aureus strains were chosen from among four-hundred S. aureus field isolates which were obtained from cows that were known to be chronically infected with bovine mastitis. Antigens from the three selected S. aureus strains showed a high variability in their electrophoretic profiles (e.g., in the range of about 21–36 kilodaltons (kD)). That is, the high electrophoretic variability demonstrated that a combination of antigens derived from the three selected strains covered most of the 397 remaining S aureus field isolates. In other words, it was expected that a vaccine containing antigens derived from the three selected strains would induce the production of antibodies that would cross react with and protect against most of the 400 isolates.

The group of 400 strains was isolated as follows: Duplicate quarter foremilk samples, obtained from cows that were known to be chronically infected with bovine mastitis, were taken aseptically according to "Laboratory methods for use in mastitis work" (International Dairy Federation, Document 132, Brussels, Belgium) and then submitted to the laboratory.

The bacteriological analysis was performed according to the standards set forth in the *Laboratory and Field Hand Book on Bovine Mastitis,* National Mastitis Council, (WI: W. H. Hoard and Sons Co., 1987). 0.01 ml from each milk sample was spread over blood-agar plates (Bacto-Agar; Difco Laboratory) containing 5% washed sheep red blood cells. The minimal detection limit was 5 colony-forming units. The Bacteria were classified as *S. aureus* according to their morphology: 1–3 mm in diameter of bacterial colony; circular, smooth, and raised with a butyrous consistency; type of hemolysis on blood agar cultivated on selective media (Baird Parker and Toluidin Blue DNase); a coagulase test (in rabbit plasma) (Coagulative enzyme); agglutination (specific antibodies against *S. aureus*) (Remel Santa Fe, Kans., U.S.A.); phage typing using the international set of typing phages for human strains (Blair and Williams, Bull. Wld. Hlth. Org. 1961, 24, 771–784). The biochemical and enzyme characterization was performed by ID-32 API STAPH (Bio Merieux Vitex, Inc., MO, U.S.A.). An antibiogram test was also performed.

In another aspect, the present invention provides a vaccine against the occurrence of bovine mastitis infection, which vaccine comprises a combination of antigens derived from the *S. aureus* strains. In an exemplary embodiment, a combination of antigens derived from the *S. aureus* strains is admixed with an adjuvant, such as an incomplete Freund's adjuvant (IFA) (Difco), for example. In another embodiment, the vaccine is a combination of 0.33 ml of each of the *S. aureus* strains with the incomplete Freund's adjuvant in a ratio of 1:1, giving a final volume of 2 ml. This vaccine protects challenged cows from udder disease following intermammary infection with *S. aureus*.

In accordance with a further aspect, the present invention provides a method for stimulating a cow's immune system to respond to an antigen derived from the *S. aureus* strains by administering a vaccine prepared in accordance with the invention. In one embodiment, the vaccine is administered to heifers about 50 to 60 days before the first parturition and then boosted (i.e., re-administered) about 30 days thereafter (i.e., after the first parturition). In another embodiment, the cows are vaccinated 30 days before the second and/or any consecutive parturition. In one embodiment, the cows are vaccinated subcutaneously (sc), under the tail root and in the area of the supra mammary lymph node.

The various aspects of the invention will now be illustrated with reference to the following non-limiting examples and the figures:

EXAMPLE 1

Separation of the *S. aureus* Crude Extract

Culture medium: Colombia broth (Difco) was modified by the addition of 0.1% d-glucose, 1% yeast extract and 0.5% NaCl. See, Lee, J. C. et al, 1987, *Infection and Immunity,* pp. 2191–2197. The medium was autoclaved at 115° C. for 15 mm., then incubated for 24–28 hr at 37° C., and then checked for the sterility of the culture.

Each of the three *S. aureus* strains (BS449, ZO3984 and VLVL8407) was grown for 24 hr at 37° C. in a 5-liter Erlenmeyer containing I liter of the medium. At the end of the growth period the broth was checked for the purity of the culture.

The BS449 and ZO3984 bacterial strains were harvested by centrifugation (3000×g, for 15 min. at 4° C.) and then washed 3 times in phosphate buffered saline (PBS) at pH 7.2.

The bacteria pellets [3.3 g/L (wet weight)] were each suspended in approximately 500 ml of PBS and subjected to mechanical agitation with glass beads by cell homogenizer (B. Braun Melsungen AG, Germany) for 10–15 minutes. The glass beads and the remaining bacteria were removed by centrifugation and discarded. The remaining solution was filtered through 0.80 and 0.45 μm-pore-size membranes. The following enzymes were added to the filtrate solution: 250 μg/100 ml of DNase and 750μg/100 ml RNase (Worthington Diagnostics, Freehold, N.J.), which was then incubated for 1 hr at 37° C. After incubation 2 ml of 0.1 mM phenylmethylsulfonyl fluoride (Sigma) in Acetone and 0.2 ml of 10 mM Tosyl (Sigma) were added to a 100 ml solution. Each solution was checked for the sterility of the culture. The protein concentrate in the solution was assayed by Braedford (Bio-Rad, UK) and according to the concentration (±0.3 mg/ml), the solution of each bacteria was aliquoted and kept at –80° C. The bacteria solutions of strains BS449 and ZO3984 were marked (BSs) and (ZOs), respectively.

The culture supernatant of the VLVL8407 strain (marked VLs) was centrifugated (3000×g for 15 mm. at 4° C.) and then filtered through 0.45 μm-pore-size membranes and finally concentrated to approximately 1:10 from the original volume. The concentration was performed in a cellulose tubular membrane (Nominal MWCO: 3500) (Cellu. Sep. Texas, USA) by Polyethylene glycol 35,000 (Fluka, Switzerland) at 4° C. At the end, the concentrate of the supernatant (VLs) was dialyzed against PBS (pH 7.2, 4° C., 48 hr). The VLs was checked for the sterility of the culture. The protein concentrate in the VLs was assayed by Braedford (Bio-Rad, UK) and according to the concentrations (±0.3 mg/ml) was aliquoted and kept at –80° C.

The antigen analysis of BSs, ZOs, and VLS was performed by polyacrylamide gel electrophoresis (PAGE) for protein (Lemili, U.K., 1970, "Cleavage of the structural proteins during the assembly of the head of bacteriophage T4", Nature, 227:680), and the glycoprotein profile was derived by an Immuno-blot kit (Bio-Rad).

EXAMPLE 2

Vaccine Preparation and Vaccination

Prior to the administration of the vaccine, antigens derived from the BSs, ZOs, and VLs were thawed, and 0.33 ml of each was mixed 1:1 with incomplete Freund's adjuvant (IFA) (Difco) to give a final volume of 2 ml/cow. Each cow was vaccinated subcutaneously (sc), 1 ml under the tail root and 1 ml in the area of the supra mammary lymph node.

The vaccine was administered to heifers about 50 to 60 days before the first parturition and then boosted (i.e., re-administered) about 30 days thereafter (i.e., after the first parturition). Cows were also vaccinated 30 days before the second parturition.

EXAMPLE 3

Toxicity and Efficacy of the Vaccines

The toxicity of the vaccine (each batch) was tested in a group of 8 mice (BALB/C). Mice were inoculated intraperitoneally (IP) with 1 ml of antigens derived from BSs, ZOs and VLs, mixed, as described above. The mice were under surveillance for 1 week. None of these mice showed any symptoms of toxicity, no mortality or morbidity.

The efficacy of the vaccine was tested by vaccinating the mice sc with 0.1 ml of the final vaccine (with IFA). The sera of the mice (prior to and post vaccination) were tested for antibodies against the BS, ZO, and VL antigens by Westernblot (Towbin, H., Staehelin, T. and Gordon, J. 1979). Electrophoretic transfer of proteins from polyacrylamide gels to nitrocellulose sheets: for procedures and some applications, see Proc. Natl. Acad. Sci., USA, 76:4350.

Illustrative results of administering the vaccine to mice are summarized in FIG. 1.

EXAMPLE 4

Two consecutive experiments were conducted, I and II. Each experiment included 10 Israeli Holstein cows in mid-lactation, yielding about 25–35 Kg/day milk free of bacterial infection or contaminated with minor pathogens and containing low Somatic Cell Counts (SCC) (<300×103/ml). In each experiment, the cows were divided into two groups according to the period of time from the last parturition, milk yield, SCC, and the status of the udder contamination. Before vaccination, blood and milk were collected from each cow and were tested for specific antibodies by immunoblot.

The cows in group 1 were vaccinated with the vaccine (BSs, ZOs, VLs mixed 1:1 with IFA, as described above). 1–1.5 ml of the vaccine was injected subcutaneously (sc) under the tail root and an additional 1–1.5 ml was administered sc in the area of the supra mammary lymph node. The cows in group 2 were injected similarly with IFA+PBS. The time of vaccination, boosts, blood collection, bacteriology examination, determination of SCC, and antibody in milk or blood are summarized in FIG. 2 for both experiments.

The cows were boosted once in Exp. I, and twice in Exp. II. The cows were challenged with 1000 CFU/quarter with *S. aureus* VLVL8407, each in two quarters. Milk and blood samples were collected during the post challenge period in order to examine the bacteriologic status, determined by SCC and antibody levels (FIG. 2).

After the termination of the experiments, sections of the injection area were submitted to histopathology.

Results

The percentage of the infected quarters and of the cows, two weeks after challenge, are summarized in FIG. 3. In Exp. II, one of the vaccinated cows was excluded before challenge due to drying off (next parturition).

In Exp. I 8/10 quarters of the control group and only 3/9 quarters in the vaccinated group were shedding *S. aureus*. In Exp. II, 11/11 quarters of the control group shed *S. aureus*, and only 3/8 in the vaccinated group did so.

Combining the two experimental groups, 19/21 quarters of the control group shed *S. aureus* while only 6/17 quarters of the vaccinated cows did so. The difference between vaccinated cows and control cows, according to the number of quarters shedding *S. aureus*, was statistically significant (P=0.001). The results are summarized in FIG. 3.

Figure 4:
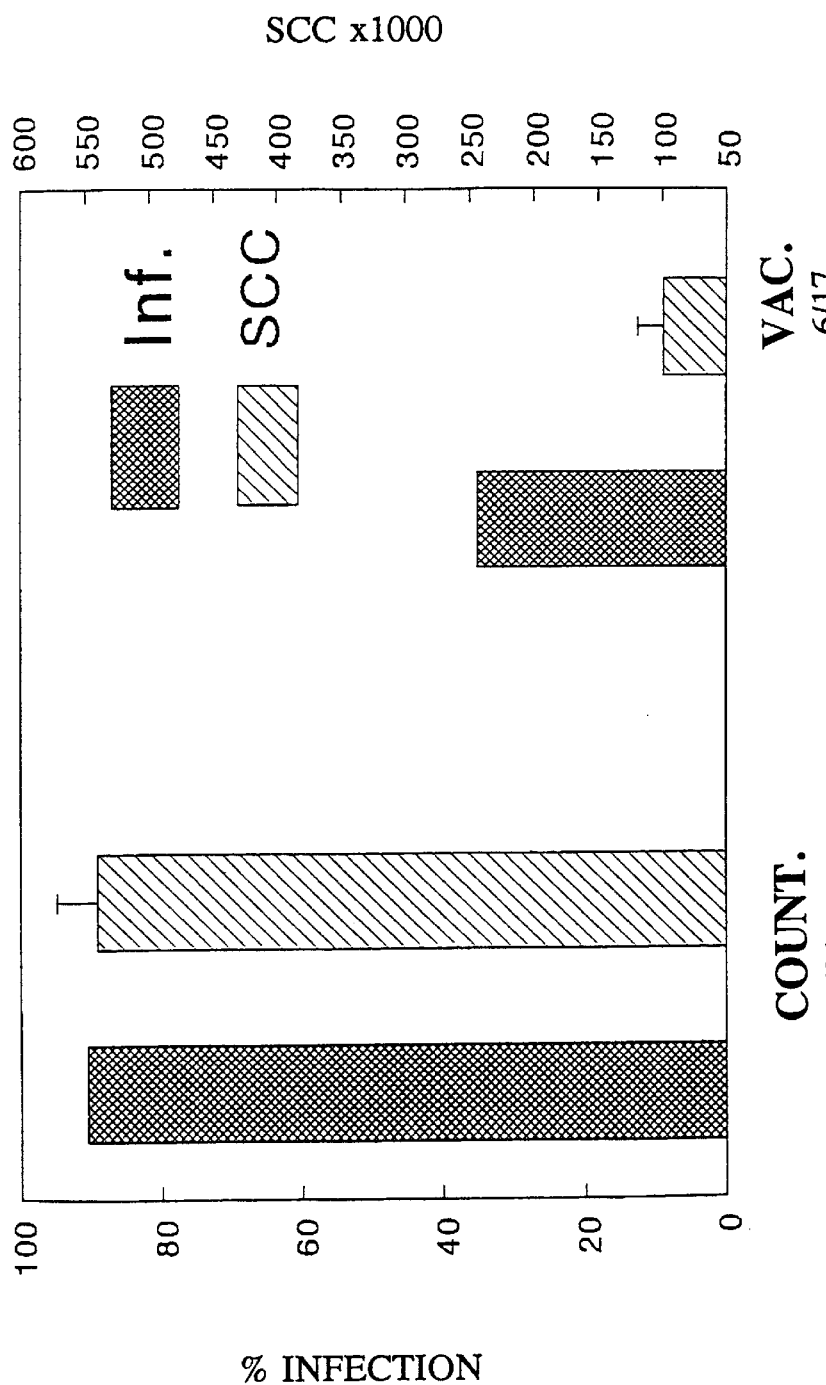
FIG. 4 is another graphical depiction of results of the studies that are the subject of FIG. 2.

Two weeks after challenge, the SCC for the quarters that shed *S. aureus* were 540×10³ (19/21) in the control group in comparison to 100×10³ (6/17) in the vaccinated group. This difference is highly statistically significant (P<0.0001). The results are summarized in FIG. 4.

The histopathological examination of the tissues around the injected area revealed normal structure with no pathological findings.

We claim:

1. A *Staphylococcus aureus* strain selected from the group consisting of *S. aureus* BS449, *S. aureus* ZO3984, and *S. aureus* VLVL8407.

2. A composition comprising a combination of at least two *Staphylococcus aureus* strains selected from the group consisting of *S. aureus* BS449, *S. aureus* ZO3984, and *S. aureus* VLVL8407.

3. The *Staphylococcus aureus* strain of claim 1, wherein said *S. aureus* BS449 is beta-hemolytic, coagulase positive and phage type 81.

4. The *Staphylococcus aureus* strain of claim 1, wherein said *S. aureus* ZO3984 is beta-hemolytic, coagulase positive and phage type 3/A, 3/C, 55 and 71.

5. The *Staphylococcus aureus* strain of claim 1, wherein said *S. aureus* VLVL8407 is non-hemolytic and coagulase positive.

6. A vaccine against the occurrence of bovine mastitis, said vaccine comprising a combination of at least two *Staphylococcus aureus* strains selected from the group consisting of *S. aureus* BS449, *S. aureus* ZO3984 and *S. aureus* VLVL8407.

7. The vaccine of claim 6, further comprising an adjuvant.

8. The vaccine of claim 7, wherein said adjuvant is an Incomplete Freund Adjuvant.

9. A method of vaccinating an animal against the occurrence of bovine mastitis, said method comprising the step of: administering to said animal a vaccine comprising a combination of antigenic compositions extracted from at least two *Staphylococcus aureus* strains selected from the group consisting of *S. aureus* BS449, *S. aureus* ZO3984, and *S. aureus* VLVL8407.

10. The method of claim 7, wherein vaccine is administered to said animal subcutaneously under the tail root and in the area of the animal's supra lymph node.

* * * * *